United States Patent [19]

Bremer et al.

[11] 4,093,635

[45] June 6, 1978

[54] PREPARATION OF MALEIC ANHYDRIDE FROM FOUR-CARBON HYDROCARBONS

[75] Inventors: Noel J. Bremer, Kent; James F. White, Akron; Ernest C. Milberger, Solon, all of Ohio

[73] Assignee: The Standard Oil Company, Cleveland, Ohio

[21] Appl. No.: 733,740

[22] Filed: Oct. 19, 1976

[51] Int. Cl.² .................................................. C07D 307/60
[52] U.S. Cl. .................................................. 260/346.75
[58] Field of Search ..................... 260/346.8 A, 346.75

[56] References Cited

U.S. PATENT DOCUMENTS

| | | | |
|---|---|---|---|
| 3,293,290 | 12/1966 | Flint et al. | 260/346.8 A |
| 3,992,419 | 11/1976 | Otaki et al. | 260/346.8 A |

OTHER PUBLICATIONS

Agasiev et al., Azerbaidzhanskii Khimicheskii Zhurnal, No. 5, (1969), pp. 128–131.

*Primary Examiner*—Henry R. Jiles
*Assistant Examiner*—Bernard Dentz
*Attorney, Agent, or Firm*—Gwenetta Douglas Hill; Herbert D. Knudsen; Larry W. Evans

[57] ABSTRACT

Maleic anhydride is produced by the oxidation of n-butane, n-butenes, 1,3-butadiene with molecular oxygen in the vapor phase in the presence of a catalytic oxide of molybdenum, phosphorus, bismuth, copper, oxygen, and a halogen selected from the group consisting of chlorine, bromine or iodine.

9 Claims, No Drawings

PREPARATION OF MALEIC ANHYDRIDE FROM FOUR-CARBON HYDROCARBONS

BACKGROUND OF THE INVENTION

Belgian Pat. No. 828,074 teaches the use of a catalyst containing phosphorus, molybdenum, bismuth, copper, at least one of Fe, Ni, Co, and K, and optionally, Li, Na, Rb, Cs, Be, Mg, Ca, Sr, or Ba in the preparation of maleic anhydride from butene-1, butene-2, butadiene, pentane, pentadiene, cyclopentadiene and benzene. Comparative Example 4, at pages 20 and 21 of this patent exemplifies that use of a catalyst having the formula $P_{1.00}Mo_{12}Bi_{0.36}Cu_{0.54}O_{39.6}$ in the oxidation of butene-1 gave a 27.9% yield of maleic anhydride, based on the amount of butene-1 fed.

French Pat. No. 1,601,955 teaches use of a catalyst having the composition $AO_3$—$B_2O_5$—$M_2O_5$—$N_xO$—$R_2O$ wherein A is Cr, Mo, W or U; B is V or Nb; M is P, As, Sb or Bi; N is Cu, Ag, Fe, Co or Ni; R is Li, Na, K, Cs or Rb. Preferred composition is 15-55 atomic %A, 30-70% B, 0-15% M, 0.1-20% N, and 0-15% R.

The present invention is a result of a search for more efficient catalysts for use in the oxidation of 1,3-butadiene to produce maleic anhydride.

The catalysts employed in the present invention are unexpectedly advantageous in the production of maleic anhydride from n-butene, n-butenes and 1,3-butadiene. Especially desirable yields of maleic anhydride are obtained from 1,3-butadiene using the catalysts of the invention.

SUMMARY OF THE INVENTION

It has now been discovered according to the present invention in the process for the production of maleic anhydride by the oxidation of n-butane, n-butenes, 1,3-butadiene or mixture thereof, with molecular oxygen in the vapor phase at a reaction temperature of about 250° C to about 600° C in the presence of catalyst, and optionally in the presence of steam, the improvement which comprises using as a catalyst a catalyst described by the formula

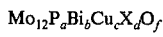

$$Mo_{12}P_aBi_bCu_cX_dO_f$$

wherein
X is a halogen selected from the group consisting of chlorine, bromine or iodine;
and wherein
$a$, $b$, and $c$ are numbers from 0.001 to 10;
$d$ is from 0.001 to 5;
$f$ is a positive number of oxygens required to satisfy the valence states of the other elements present.

Especially high yields and selectivities of maleic anhydride are obtained from four-carbon hydrocarbons in an efficient, convenient, and economical manner at a relatively low temperature. The exotherm of the reaction is low, thereby, allowing easy reaction control.

The most significant aspect of the present invention is the catalyst employed. The catalyst may be any of the catalysts delineated by the above formula. The catalysts may be prepared by a number of different techniques described in the art, such as co-precipitation of soluble salts and evaporative drying.

The catalysts of the invention have preferred limitations on their composition. Preferred are catalysts wherein $a$, $b$, and $c$ are numbers from 0.01 to 5 and $d$ is from 0.001 to 1.0. Also preferred are catalysts wherein $a$ is 0.5 to 1.5, catalysts wherein $b$ is 0.1 to 1.0, catalysts wherein $c$ is 0.1 to 1.0, and catalysts wherein $d$ is 0.01 to 0.5. Catalysts of particular interest are described wherein $d$ is 0.005 to 0.1. Especially preferred are catalysts wherein X is chlorine.

The preferred procedure of this invention involves preparing the catalysts in an aqueous slurry or solution of compounds containing molybdenum and phosphorus, adding the remaining components; and evaporating this aqueous mixture. Suitable molybdenum compounds that may be employed in the preparation of the catalysts delineated by the above formula include molybdenum trioxide, phosphomolybdic acid, molybdic acid, and ammonium heptamolybdate. Excellent results are obtained using catalysts of the invention wherein at least part of the molybdenum employed in the preparation of the catalysts is supplied in the form of molybdenum trioxide. Suitable phosphorus compounds that may be employed in the preparation of the catalysts include orthophosphoric acid, metaphosphoric acid, triphosphoric acid, phosphorus halides or oxyhalides. The remaining components of the catalysts may be added as oxide, acetate, formate, sulfate, nitrate, carbonate, halide and oxyhalide. Especially preferred are catalysts wherein bismuth is supplied in the form of a bismuth halide or oxyhalide.

Excellent results are obtained by refluxing phosphoric acid and molybdenum trioxide in water for about 1.5 to 3 hours, however, commercial phosphomolybdic acid may be effectively utilized; adding the remaining components to the aqueous slurry and boiling to a thick paste, where at least one of the components is added as a halide or oxyhalide; and drying at 110° C to 120° C in air. It is not clearly understood where the halogen atom is located in the catalytic structure. Infra-red analysis reveals that the catalysts are mostly phosphomolybdate-based and that the halogen is most probably present as a molybdenum oxyhalide.

By the preferred procedure of the invention, calcination of the catalysts is not generally required to obtain desired catalysts described within the above formula. However, calcination may be accomplished by heating the dry catalytic components at a temperature of about 300° C to about 700° C, with preferred calcination being accomplished at a temperature of 325° C to 450° C. The hydrocarbon reacted may be n-butane, n-butenes, 1,3-butadiene or a mixture thereof. Preferred is the use of 1,3-butadiene or a mixture of hydrocarbons that are produced in refinery streams. The molecular oxygen is most conveniently added as air, but synthetic streams containing molecular oxygen are also suitable. In addition to the hydrocarbon and molecular oxygen, other gases may be added to the reactant feed. For example, steam or nitrogen could be added to the reactants.

The ratio of the reactants may vary widely and are not critical. The ratio of the hydrocarbon to molecular oxygen may range from about 2 to about 30 moles of oxygen per mole of hydrocarbon. Preferred oxygen ratios are about 4 to about 20 moles per mole of hydrocarbon.

The reaction temperature may vary widely and is dependent upon the particular hydrocarbon and catalyst employed. Normally, temperatures of about 250° C to about 600° C are employed with temperatures of 250° C to 450° C being preferred.

The catalyst may be used alone or a support could be employed. Suitable supports include silica, alumina, Alundum, silicon carbide, boron phosphate, zirconia, and titania. The catalysts are conveniently used in a fixed-bed reactor using tablets, pellets or the like or in a fluid-bed reactor using a catalyst preferably having a particle size of less than about 300 microns. The contact time may be as low as a fraction of a second or as high as 20 seconds or more. The reaction may be conducted at atmospheric, superatmospheric or subatmospheric pressure.

Excellent results are obtained using a coated catalyst consisting essentially of an inert support material having a diameter of at least 20 microns and an outer surface and a continuous coating of said active catalyst on said inert support strongly adhering to the outer surface of said support.

By use of these coated catalysts in the reaction to produce maleic anhydride, a very low exotherm is realized allowing for better control of the reaction. High single pass yields are exhibited and the elimination of undesirable byproducts is obtained.

The special coated catalyst consists of an innersupport material having an outside surface and a coating of the active catalytic material on this outside surface. These catalysts can be prepared by a number of different methods.

The support material for the catalyst forms the inner core of the catalyst. This is an essentially inert support and may have substantially any particle size or shape although a diameter of greater than 20 microns is preferred. Especially preferred in the present invention for use in a commercial reactor are those supports which are spherical and which have a diameter of about 0.2 cm. to about 2 cm. Suitable examples of essentially inert support materials include: Alundum, silica, alumina, alumina-silica, silicon carbide, titania and zirconia. Especially preferred among these supports are Alundum, silica, alumina and alumina-silica.

The catalysts may contain essentially any proportions of support and catalytically active material. The limits of this relationship are only set by the relative ability of the catalyst and support material to accommodate each other. Preferred catalysts contain about 10 to about 100 percent by weight of catalytically active material based on the weight of the support.

The preparation of these coated catalysts can be accomplished by various techniques. The basic method of preparing these catalysts is to partially wet the support material with a liquid. The support should not be wet on the outside surface of the total mass. It should appear to be dry to the touch. If the support is wet, then the active catalytic material may agglomerate into separate aggregates when coating of the support is attempted. These partially wet supports are then contacted with a powder of the catalytically active material and the mixture is gently agitated until the catalyst is formed. The gentle agitation is most conveniently conducted by placing the partially wet support in a rotating drum or jar and adding the active catalytic material. This is very economically done.

Using the catalysts of the invention in the preparation of maleic anhydride, excellent yields are obtained in a convenient reaction with low amounts of by-products.

SPECIFIC EMBODIMENTS

A catalyst of the formula $Mo_{12}P_{1.32}Bi_{0.5}Cu_{0.25}Cl_{0.06}O_f$ was prepared as follows: A slurry was prepared of 86.4 grams (0.60 mole Mo) of molybdenum trioxide and 7.6 g. (0.067 mole P) of 85% phosphoric acid in 500 mls. of distilled water; boiled with stirring for three hours to form phosphomolybdic acid which was yellowish green in color. To this slurry was added 2.5 g. (0.0125 mole Cu) of copper acetate; no change in color, followed by the addition of 7.9 g. (0.025 mole Bi) of bismuth chloride dissolved in 4.0 ml. of concentrated hydrochloric acid. The mixture was boiled to dryness; dried overnight at 110° C in air. The catalyst was ground and screened to 10/30 mesh fraction.

A portion of the catalyst particles were charged to a 20 cc. fixed-bed reactor equipped with a 1.02 cm. inside diameter stainless steel tube.

The reactor was heated to reaction temperature under a flow of air and a feed of 1,3-butadiene/air, as indicated below, was fed over the catalyst at an apparent contact time of 3 to 4 seconds and the performance evaluated by collecting and analyzing the products.

The results of these experiments appear in the TABLE below. The following definitions are used in measuring the carbon atoms in the feed and in the product:

% Single pass yield = $\dfrac{\text{Moles of Maleic Anhydride Recovered}}{\text{Moles of Hydrocarbon in the Feed}} \times 100$ Total Conversion = $\dfrac{\text{Moles of Hydrocarbon Reacted}}{\text{Moles of Hydrocarbon in the Feed}} \times 100$ Selectivity = $\dfrac{\text{Single Pass Yield of Maleic Anhydride}}{\text{Single Pass Yields of Total Acid}} \times 100$

TABLE

Preparation of Maleic Anhydride From 1,3-butadiene Using The Catalyst $Mo_{12}P_{1.32}Bi_{0.5}Cu_{0.25}Cl_{0.06}O_f$

| Temp. ° C. | | Feed Ratio | Results, % | | |
|---|---|---|---|---|---|
| Bath | Exotherm | Air/HC | Total Acid | Maleic Anhydride | Selectivity |
| 301 | 310 | 23 | 8.31 | 6.97 | 83.9 |
| 317 | 329 | 41 | 48.10 | 44.09 | 91.7 |
| 333 | 351 | 34 | 53.47 | 47.88 | 89.6 |
| 349 | 379 | 27 | 52.67 | 47.07 | 89.4 |

In the same manner catalysts containing different amounts of phosphorus, bismuth, copper and chlorine are used to prepare maleic anhydride from 1,3-butadiene.

Also, in the same manner, various catalysts of the invention are promoted with elements such as Mn, Rh, Ru, Ti, Zn, Re, Pb, rare earth element, In, Sn, Zr, Cr, Pd or mixture thereof to produce desirable yields of maleic anhydride from n-butane, n-butenes, 1,3-butadiene or mixture thereof.

We claim:

1. In a process for the preparation of maleic anhydride by the oxidation of n-butane, n-butenes, 1,3-butadiene or mixture thereof with molecular oxygen in the vapor phase at a reaction temperature of about 250° C to 600° C in the presence of a catalyst, the improvement comprising using as a catalyst a catalyst which is free of iron, cobalt, nickel, an alkali metal and an alkaline earth metal, said catalyst having the formula $Mo_{12}P_aBi_bCu_cCl_dO_f$ wherein a, b and c are numbers from 0.001–10;

d is from 0.001–5;

and $f$ is a positive number of oxygens required to satisfy the valence states of the other elements present.

2. The process of claim 1 wherein $a$, $b$, and $c$ are numbers from 0.01 to 5 and $d$ is from 0.001 to 1.0.

3. The process of claim 1 wherein $a$ is 0.5 to 1.5.

4. The process of claim 1 wherein $b$ is 0.1 to 1.0.

5. The process of claim 1 wherein $c$ is 0.1 to 1.0.

6. The process of claim 1 wherein $d$ is 0.005 to 0.1.

7. The process of claim 1 wherein $d$ is 0.01 to 0.5

8. The process of claim 1 wherein the catalyst employed is $Mo_{12}Bi_{0.5}P_{1.32}Cu_{0.25}Cl_{0.06}O_f$.

9. In a process for the preparation of maleic anhydride by the oxidation of 1,3-butadiene with molecular oxygen in the vapor phase at a reaction temperature of about 250° C to 600° C in the presence of a catalyst, the improvement comprising using as a catalyst a catalyst which is free of iron, cobalt, nickel, an alkali metal and an alkaline earth metal, said catalyst having the formula $$Mo_{12}P_aBi_bCu_cX_dO_f$$

wherein
  X is a halogen selected from the group consisting of chlorine, bromine or iodine; and
wherein
  $a$, $b$ and $c$ are numbers from 0.001–10;
  $d$ is from 0.001–5;
  and $f$ is a positive number of oxygens required to satisfy the valence states of the other elements present.

* * * * *